United States Patent
Baughman et al.

(10) Patent No.: US 10,831,274 B2
(45) Date of Patent: Nov. 10, 2020

(54) CHANGING TACTILE SENSITIVITY OF INTERACTIONS WITH MIDAIR INTERFACES

(71) Applicant: International Business Machines Corporation, Armonk, NY (US)

(72) Inventors: Aaron K. Baughman, Silver Spring, MD (US); Aaron R. Cox, Austin, TX (US); John J. Kent, North Attleboro, MA (US); Stephen C. Hammer, Marietta, GA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 141 days.

(21) Appl. No.: 15/973,520

(22) Filed: May 7, 2018

(65) Prior Publication Data
US 2019/0339774 A1 Nov. 7, 2019

(51) Int. Cl.
*G06F 3/01* (2006.01)
*G06F 3/043* (2006.01)
(Continued)

(52) U.S. Cl.
CPC .............. *G06F 3/016* (2013.01); *G06F 3/043* (2013.01); *G06F 30/20* (2020.01); *A61B 8/06* (2013.01);
(Continued)

(58) Field of Classification Search
CPC .... G03H 3/00; G03H 2001/0061; G03H 5/00; G03H 2210/30; G06F 3/043; G06F 3/016;
(Continued)

(56) References Cited

U.S. PATENT DOCUMENTS

| 5,889,870 A | 3/1999 | Norris |
| 9,251,676 B2 | 2/2016 | Taylor et al. |

(Continued)

FOREIGN PATENT DOCUMENTS

KR  940007909 B1  8/1994

OTHER PUBLICATIONS

Petrofsky et al, Interrelationship between Air Temperature applied to the skin: The resultant response on blood flow, Apr. 1, 2012, Medical Science Monitor, 2012 18(4), CR201-208 (Year: 2012).*
(Continued)

*Primary Examiner* — Patrick N Edouard
*Assistant Examiner* — Douglas M Wilson
(74) *Attorney, Agent, or Firm* — Garg Law Firm, PLLC; Rakesh Garg; James Nock

(57) ABSTRACT

A reflection is captured of a subsonic signal reflected by a contact surface. The contact surface is contacting a simulated surface of an object projected from a midair interface (MAI) device. A difference between the subsonic signal and the reflection is converted into a measurement of a flow in the contact surface. When the measurement is in a range of measurements, a change is caused in a temperature of a volume of a medium, the simulated surface being projected in volume of the medium, where the change in the temperature causes a second change in the flow in the contact surface.

19 Claims, 8 Drawing Sheets

(51) Int. Cl.
- *G06F 3/0484* (2013.01)
- *G06F 3/0481* (2013.01)
- *G06T 19/00* (2011.01)
- *G03H 1/00* (2006.01)
- *G03H 3/00* (2006.01)
- *A61B 8/06* (2006.01)
- *A61B 8/08* (2006.01)
- *G06F 30/20* (2020.01)
- *G03H 5/00* (2006.01)

(52) U.S. Cl.
CPC .............. *A61B 8/488* (2013.01); *G03H 3/00* (2013.01); *G03H 5/00* (2013.01); *G03H 2001/0061* (2013.01); *G03H 2210/30* (2013.01); *G06F 3/011* (2013.01); *G06F 3/04815* (2013.01); *G06F 3/04847* (2013.01); *G06T 19/00* (2013.01); *G06T 2219/012* (2013.01)

(58) Field of Classification Search
CPC ...... G06F 3/011; G06F 3/04847; G06F 3/015; G01G 1/663; Y10T 137/0324; A61B 8/488; A61B 8/06; A61B 5/026; A61B 2562/0204; A61B 8/466; A61N 1/36031; A61H 2201/025; A61H 2205/065; G01P 5/00; G01F 1/7082; G10K 15/00
See application file for complete search history.

(56) References Cited

U.S. PATENT DOCUMENTS

| | | | |
|---|---|---|---|
| 2010/0280691 | A1 | 11/2010 | Eckhoff et al. |
| 2015/0015607 | A1* | 1/2015 | Sodhi ................. G06F 3/0425 345/633 |
| 2017/0018171 | A1 | 1/2017 | Carter et al. |
| 2017/0068213 | A1* | 3/2017 | Rhee ..................... G06F 3/011 |
| 2017/0123499 | A1* | 5/2017 | Eid ........................ G10K 15/00 |
| 2017/0177085 | A1* | 6/2017 | Sun ........................ G06F 3/012 |
| 2018/0018016 | A1* | 1/2018 | Shi ........................ A61B 8/488 |

OTHER PUBLICATIONS

International Searching Aiithority, PCT/IB2019/053027, dated Jul. 3, 2019.
Rabin et al; Tactile/proprioceptive integration during arm localization is intact in individuals with Parkinson's disease, Feb. 5, 2011.
Cordo et al; Proprioceptive consequences of tendon vibration during movement, Oct. 1995;74(4):1675-88.
Kigawa et al; Proprioceptive Interaction between the Two Arms in a Single-Arm Pointing Task, Aug. 28, 2015.
Gandevia; Proprioception—the sixth sense, Oct. 1, 2017.
Bau; TeslaTouch: Electrovibration for Touch Surfaces, 2010.
Ultrahaptics; Discover a new type of haptics, 2018.
Disney; Research Areas, 2018.
List of IBM related applications, Appendix P, 2018.

* cited by examiner

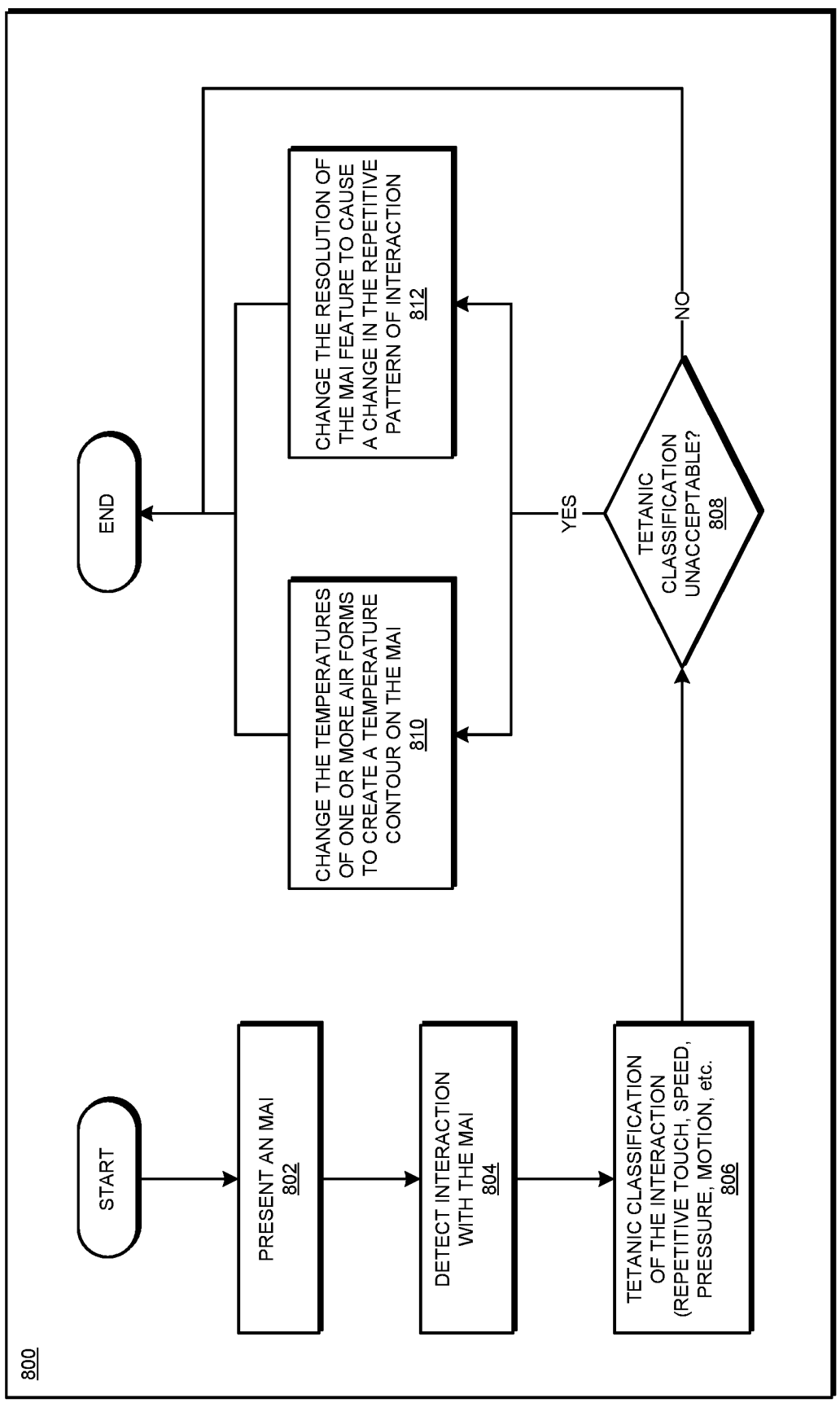

CHANGING TACTILE SENSITIVITY OF INTERACTIONS WITH MIDAIR INTERFACES

TECHNICAL FIELD

The present invention relates generally to a method, system, and computer program product for simulations of physical objects using holograms and interactions with such simulated objects. More particularly, the present invention relates to a method, system, and computer program product for changing tactile sensitivity of interactions with a midair interface.

BACKGROUND

A midair interface (MAI) is a simulation of a solid three-dimensional physical object in a medium, such as air, by projecting a shape in the medium. Upon touching, the simulated object feels like the three-dimensional physical object in some respects. The projections in the medium are holographic projections (holograms), where the tactile properties are achieved by forming the projection using ultrasonic sound waves in the medium. A hologram formed by projecting sound into a medium may or may not present a visual rendering of the simulated object but are capable of providing a touch sensation, i.e., tactile feedback when interacting with the simulated object.

It is also possible to produce holograms using light or laser projections into a medium. Light-based holograms may be better at visual rendering of the simulated object but generally lack the capability to provide tactile feedback when interacting with the simulated object.

For the purposes of the illustrative embodiments, a hologram or simulation that is capable of providing tactile feedback is the MAI used and described herein. In other words, the MAI contemplated within the scope of the illustrative embodiments are similar to the holographic projections formed using sound waves to control the pressure in a medium or using pressure-controlled columns of the medium.

For example, a MAI simulated keyboard using air medium presents physical keys of a physical keyboard in midair, such that a tactile interaction with the simulated keys induces the brain of a human user (or a cognitive system of a humanoid) to cognitively perceive physical keys in midair. A MAI simulated key can be depressed and released in a manner similar to a physical key of a physical keyboard, by applying and releasing finger pressure against one or more projections that are shaping the air medium like a physical key.

A simulated key of the example is different from a physical key of the example physical keyboard in that a finger cannot normally puncture and go through a physical key whereas the finger can continue pressing the simulated key to eventually go through the simulated key. Other simulated objects are generally representative of the physical shape, size, and tactile feel of a corresponding physical object but are non-solid unlike the corresponding physical object and similarly puncturable due to the non-solid nature of the medium that is used to form the simulated object.

For the clarity of the description and without implying any limitation thereto, air is assumed to be the medium when describing various operations and embodiments. Other media, such as water or a different gas or fluid can similarly be used in the manner of a described operation or embodiment without departing the scope of the illustrative embodiments. Additionally, for the purposes of the clarity of the description and without implying any limitation on the illustrative embodiments, a human user is assumed to be interacting with an MAI. From this disclosure, those of ordinary skill in the art will be able to adapt an embodiment to operate in a similar manner with a humanoid or a machine that operates as a user of an MAI, and such adaptations are contemplated within the scope of the illustrative embodiments.

Devices are presently available to project holograms in air to form simulated objects of an MAI. For example, a device consisting of a grid of projection nozzles is presently available to form simulated objects above the device by adjusting jets of air projecting from the device towards a volume of air above the device.

A volume of air, which is shaped, formed, or pressure-adjusted using sound or other methods, to form an entirety or a portion of a simulated object for MAI is referred to herein as an "air form." An object or a portion thereof, simulated using one or more air forms is referred to herein as a simulated object, midair simulated shape, or variations of these phrases, unless expressly distinguished where used.

A midair interaction with an MAI is a manipulation of a simulated object in the MAI using tactile operations. For example, a simulated key can be touched, depressed, and released; a simulated ball can be held, turned, or squeezed; and a simulated graph can be touched, rubbed, or pushed, by application of physical force against the simulated object. A midair interaction induces a cognitive perception of a tactile feeling. When a human is interacting with the MAI, the interactions with the MAI cause the tactile perception to be a cognitively induced in a human brain. The human brain is a type of cognitive receptor. When a humanoid or machine is interacting with the MAI, the interactions with the MAI cause the tactile perception to be a cognitively induced in an appropriate cognitive receptor unit associated with the humanoid or machine. Hereinafter, a reference to cognitive induction is a reference to a tactile perception that results from physical interaction with a simulated object produced by an MAI, and which can be received and processed by the appropriate receptor.

SUMMARY

The illustrative embodiments provide a method, system, and computer program product. An embodiment includes a method that captures a reflection of a infrasonic signal, the infrasonic signal being reflected by a contact surface, wherein the contact surface is contacting a simulated surface of an object projected from a midair interface (MAI) device. The embodiment converts a difference between the infrasonic signal and the reflection into a measurement of a flow in the contact surface. The embodiment causes, responsive to the measurement being in a range of measurements, a change in a temperature of a volume of a medium, the simulated surface being projected in volume of the medium, wherein the change in the temperature causes a second change in the flow in the contact surface.

An embodiment includes a computer usable program product. The computer usable program product includes a computer-readable storage device, and program instructions stored on the storage device.

An embodiment includes a computer system. The computer system includes a processor, a computer-readable memory, and a computer-readable storage device, and program instructions stored on the storage device for execution by the processor via the memory.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

FIG. 8 depicts a flowchart of another example process for changing tactile sensitivity of interactions with a midair interface in accordance with an illustrative embodiment.

DETAILED DESCRIPTION

Figure 1:
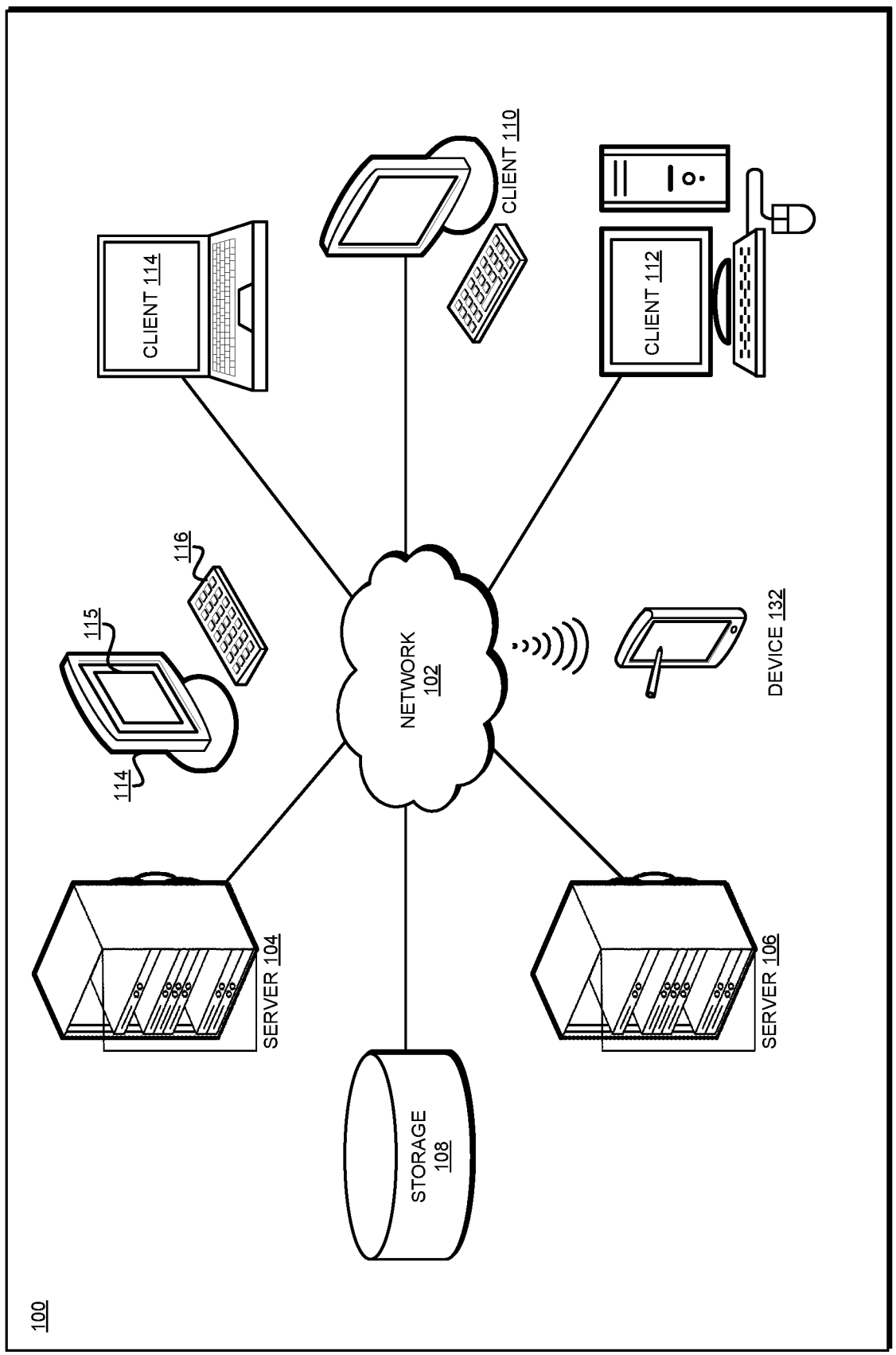
FIG. 1 depicts a block diagram of a network of data processing systems in which illustrative embodiments may be implemented.

Human-machine interfaces are a well-recognized technological field of endeavor. Computers and other machines require inputs from users and provide outputs to users via such human-machine interfaces. Computer keyboards, computer mouse or other pointing devices, digital stylus or similar writing instruments, touchscreens, and the like are common examples of human-machine interfaces for providing inputs. Some interfaces, such as a touchscreen or a pointing device, can provide tactile feedback through vibrations, change of textures, change of required force, change of pressure, and the like.

Projection of, and detecting interactions with, midair interfaces as an alternative human-machine interface is also a well-recognized technological field of endeavor. The present state of the technology in this field of endeavor has certain drawbacks and limitations. The operations of the illustrative embodiments impart additional or new capabilities to improve the existing technology in the technological field of endeavor of human-machine interfaces, especially in the area of midair interfaces.

The illustrative embodiments recognize that midair interfaces suffer from certain drawbacks. As one example, human users of MAIs have found that fingers, arms, and other extremities of the human body that are engaged when interacting with an MAI tend to become numb or progressively degraded in their sensation perceiving capabilities over a period of interactions. For example, it has been observed that an arm suspended in the air above an MAI device will start to fall numb over a period of suspension. The reduced sensitivity to tactile sensation at the finger tips also degrades as a result.

It has also been found that repetitive touching, pressing, rubbing, or other tactile manipulation of surfaces also tends to induce a progressive reduction in tactile sensitivities of the extremities being used. For example, if a user repeatedly touches or rubs a textured surface, the user's perception of the texture is known to degrade after a period of such tactile activity. This observation is true whether the surface is an actual physical surface or a simulated surface of a MAI.

The surface of a user's extremity that contacts an MAI for performing tactile operations is referred to herein as a "contact surface" unless expressly distinguished. A surface of a simulated object that is touched by a contact surface is referred to herein as an "object surface" unless expressly distinguished.

These and other degradation of tactile perception at the contact surface are disadvantages of using the presently available MAIs. The present state of the technological field of endeavor of human-machine interface via MAIs presently does not address or mitigate the degradation of tactile perception. A need exists for detecting the degradation of tactile perception while using an MAI. A need exists to prevent or mitigate such degradation. A need exists to restore the tactile perception sensitivity, if degraded.

The illustrative embodiments recognize that the presently available tools or solutions do not address these needs/problems or provide adequate solutions for these needs/problems. The illustrative embodiments used to describe the invention generally address and solve the above-described problems and other related problems by changing tactile sensitivity of interactions with a midair interface.

A device capable of projecting an MAI consisting of simulated objects formed using air forms is contemplated. Such a device is referred to herein as an MAI device. A prior-art MAI device can be modified using an embodiment to form a modified MAI device. To form a modified MAI device, an embodiment can be implemented as a combination of certain hardware components, e.g., the prior-art MAI device, and a software application. An implementation of an embodiment, or one or more components thereof, can be configured as a modification of an existing MAI device, with a companion software application executing in some combination of (i) the MAI device itself, (ii) a data processing system communicating with the MAI device over short-range radio or a local area network (LAN), and (iii) a data processing system communicating with the MAI device over a wide area network (WAN).

Projection nozzles are arranged in a two-dimensional array in a prior-art MAI device. The projection nozzles project air forms into a volume of air, and the projections form a simulated object. An air form can be thought of as a single pixel or a group of pixels (or an equivalent thereof) that render a portion of an object surface of the simulated object. One or more simulated objects together forms the MAI.

To form one embodiment of the modified MAI device, an embodiment adds additional components in the array of projection nozzles. In one embodiment, for each projection nozzle, the embodiment configures a infrasonic transducer (SST) within the projection nozzle or in proximity with the projection nozzle.

The SST is configured to emit a sound output (infrasonic signal) where the frequency of the sound is below the audible range of frequencies for humans (hence, "infrasonic"). The SST is further configured to receive as input a reflection of the emitted infrasonic signal. The SST may be an additional infrasonic component or a modification of an existing sound component to operate in the infrasonic frequency range in a manner described herein.

Furthermore, the SST is so configured that the SST projects a infrasonic signal into the air form or substantially at the same pixel or group of pixels represented by the air form. As a consequence of such a configuration, if a contact surface, e.g., a fingertip of a human user, manipulates the portion of the object surface formed using the air form, the emitted infrasonic signal bounces off the contact surface and is received by the SST.

In one embodiment, the transmitter of the infrasonic signal and the receiver of the reflection can be distinct apparatus located at different physical locations relative to the corresponding projection nozzle on the modified MAI device. In another embodiment, the transmitter of the infrasonic signal and the receiver of the reflection are co-located at substantially the same physical location relative to the corresponding projection nozzle on the modified MAI device.

infrasonic sound is presently used to measure liquid flows. Measurement techniques and apparatus presently exist to compute a difference between a transmitted infrasonic signal and a reflection of that signal from a surface and to translate the difference into a flow measurement. In other words, a difference between the transmitted and the reflected infrasonic signal has a correspondence with an amount of flow of a liquid at or near the surface from which the signal reflects. In one example case, the difference may be a difference in the transmitted and received frequencies. In another example case, the difference may be a difference in the signal strength of the transmitted and received signals. In another example case, the difference may be a difference in a phase of transmitted signal and a phase of the received signal.

Using such a technique, an embodiment measures an amount of blood flowing in the capillaries situated at or near a contact surface. The embodiment determines from the flow measurement whether the flow volume can be regarded as normal, low, or high relative to an acceptable range of flow for a given user and the particular contact surface.

An embodiment regards a flow as normal when the flow measurement is within a range defined by, and inclusive of, two thresholds. The embodiment regards a flow as low when the flow measurement is below the lower of the two thresholds. The embodiment regards a flow as high when the flow measurement is above the higher of the two thresholds.

The embodiment further regards a low flow as an indication of degraded tactile perception, or reduced sensitivity to tactile input at the contact surface, such as caused by numbness of an extremity. The embodiment also regards a high flow as an indication of degraded tactile perception, such as that caused by inflammation of an extremity from repetitive tactile operations by the contact surface.

An embodiment adds a thermal element in conjunction with a projection nozzle as a part of forming the modified MAI device. In one embodiment, the thermal element is associated with a single projection nozzle and is collocated with the nozzle at substantially the same location as the location of the nozzle. In another embodiment, the thermal element is associated with a plurality of projection nozzles and is located in close proximity—substantially the same area on the MAI device—as the group of projection nozzles. In another embodiment, the thermal element is located at a different location than the location of the projection nozzle, such as at the periphery of the modified MAI device.

In one embodiment, the thermal element is configured to increase or decrease the temperature of air into which a nozzle projects an air form. In another embodiment, the thermal element is configured to only increase the temperature of the air into which a nozzle projects an air form.

When an embodiment detects a low blood flow through infrasonic measurements described herein, the embodiment activates the thermal element to increase the temperature of the air. Particularly, the embodiment activates those thermal elements which are configured to heat that volume of air where one or more selected projection nozzles are projecting air forms, such that those air forms are forming the object surface where contact with the contact surface is occurring. Such activation is selective and may not activate the thermal elements of other projection nozzles that are projecting other portions of the simulated object where those portions are not being manipulated by the contact surface.

The increase in the air temperature at or near the object surface causes the contact surface temperature to also increase during tactile manipulations of the object surface. The increased temperature of the contact surface results in an increase in the blood flow to the contact surface and a resulting decrease in the numbness at the contact surface, at an extremity related to the contact surface, or both. The decreased numbness improves tactile sensitivity of the contact surface.

When an embodiment detects a high blood flow through infrasonic measurements described herein, and when the thermal element is configured for cooling the air as well, the embodiment activates the thermal element to decrease the temperature of the air. Particularly, the embodiment activates those thermal elements which are configured to cool that volume of air where one or more selected projection nozzles are projecting air forms, such that those air forms are forming the object surface where contact with the contact surface is occurring. Such activation is selective and may not activate the thermal elements of other projection nozzles that are projecting other portions of the simulated object where those portions are not being manipulated by the contact surface.

The decrease in the air temperature at the object surface causes the contact surface temperature to also decrease during tactile manipulations. The decreased temperature of the contact surface results in a decrease in the blood flow at the contact surface. The reduced blood flow results in a decrease in the inflammation at the contact surface, at an extremity related to the contact surface, or both. The decreased inflammation improves and/or restores a level of tactile sensitivity of the contact surface.

Another embodiment configures the projection nozzle to increase or decrease a resolution of the air form. The illustrative embodiments recognize that when a large area of the contact surface is used for tactile interaction with a simulated object, the nerve endings in the large area are all activated to sense the touch sensation. Thus, when the contact surface becomes numb or inflamed, all the nerve endings in the entire area are adversely affected together, i.e., they all experience decreases tactile sensitivity.

When an embodiment detects indicators of degraded tactile sensitivity in a contact surface, the embodiment causes the projection nozzle to reshape the air form such that the air form projects a smaller object surface area as compared to the size of the object surface area being projected when the degraded tactile sensitivity is detected. The smaller area causes a smaller group of nerve endings to engage in the tactile sensation at a given time, allowing other non-engaged nerve endings time to recover.

The changing of the resolution by reshaping the air form can be accomplished in a variety of ways. For example, one embodiment constricts or enlarges a nozzle opening to change the size of the air form—and consequently the resolution of the feature projected by the air form. Another embodiment obstructs or un-obstructs an air form without changing the nozzle characteristics. The obstruction or removal of obstructions from the path of the air form through air causes the size of the air flow to change resulting in the changed resolution. Another embodiment raises or lowers a projection nozzle relative to the contact surface to change a distance between the nozzle opening and the contact surface. Increasing the path of the air flow cause the feature resolution to decrease (become coarser in resolution or granularity). Conversely, decreasing the path of the air flow cause the feature resolution to increase (become finer in resolution or granularity). Thus, the changed path distance of the air flow results in the changed resolution.

When a feature, such as a texture or contour of the object surface, is presented over a relatively larger surface, the user may have difficulty perceiving the feature. For example, a height difference of 0.1 inch in a feature may not be perceptible with degraded tactile sensitivity if the feature were projected in an area of 1 square inch. But, the same height difference of 0.1 inch in the feature may be perceptible even with degraded tactile sensitivity if the feature were projected in an area of 0.1 square inches.

Thus, the change in the resolution, i.e., the embodiment causing a projected feature to appear in a relatively smaller area as compared to a previous projection of the same feature, increases a tactile perception of the feature. Additionally, the higher resolution—i.e., the embodiment causing a projected feature to appear in a relatively smaller area, also allows for more detailed features to be accommodated in the same area as compared to lower resolution projections. The sizes of the areas and the resolutions of the features are described in comparison to one another, and not relative to any absolute size or standard.

The illustrative embodiments recognize that that a numb arm or leg falls numb when positioned in the same position for a period and can regain its tactile sensitivity when moved to a different position.

Another embodiment causes the user to move an extremity associated with a contact surface to change the blood flow (and the resulting numbness) at the contact surface. The embodiment induces a movement by creating a temperature contour on the simulated object.

For example, suppose that the surface of the simulated object comprises areas A, B, and C, where area A is adjacent to area B and area B is adjacent to area C. Further suppose that the user has been resting the contact surface, or positioning the contact surface repeatedly, at area A, which forms the present object surface. Further assume that moving the contact surface from area A to areas B or C has no adverse effect on the underlying command or operation being performed by the tactile manipulations.

The embodiment determines that the user should be induced to reposition the contact surface from area A to area C on the simulated object. The embodiment further determines, e.g., through machine learning from previous MAI interactions of the user, or from other methods, that the user exhibits a dislike for hot surfaces—i.e., surface having a temperature of greater than and including an upper threshold temperature, and exhibits a liking for cold surfaces—i.e., surface having a temperature of less than a different lower threshold temperature.

Accordingly, the embodiment causes the air volume of the air forms from the nozzles projecting area A to heat up to a temperature greater than the upper threshold. The embodiment causes the air flow from the nozzles projecting area B to be at a temperature between the upper and the lower thresholds. The embodiment causes the air flow from the nozzles projecting area C to be at a temperature less than the lower threshold. By adjusting the temperatures of the air forms forming areas A, B, and C, the embodiment constructs a thermal contour or temperature contour of progressively decreasing temperatures from area A to area C.

The midair contour of the projected surface of the simulated object remains unchanged but the thermal contour of the surface changes in this manner. The user, who prefers colder temperatures is thus induced to reposition the contact surface from area A to area B and from area B to area C. This repositioning causes the movement of the extremity. The movement of the extremity assists in regaining the tactile sensitivity in the extremity and/or the contact surface.

The illustrative embodiments also recognize that tetanic contractions or tetanic spasms can cause an extremity, such as a finger, to make a rapid repeated motion. The illustrative embodiments recognize that tetanic movements can cause a user to repeatedly touch a simulated surface.

An embodiment detects a repeated contact of a user's extremity with a simulated surface. The embodiment classifies the rapidity of the user's contact with the simulated surface according to a predetermined set of tetanic classifications. Some tetanic classifications—i.e., some speed of rapid repeated contacts—are acceptable and some are not. If the embodiment determines that the rapid repeated contact falls into an unacceptable tetanic classification, the embodiment induces a movement in the extremity. The embodiment uses either a temperature contour method or a change of resolution method, as described herein, to induce the movement.

The manner of changing tactile sensitivity of interactions with a midair interface described herein is unavailable in the presently available methods in the technological field of endeavor pertaining to human-machine interface, particularly in the field of MAIs. A method of an embodiment described herein, when implemented to execute on a device or data processing system, comprises substantial advancement of the functionality of that device or data processing system in improving tactile sensitivity and feature projection in MAIs.

The illustrative embodiments are described with respect to certain types of MAI devices, media, volumes, media forms, users, simulated objects, contact surfaces, fluid flows, temperatures, feature projections, repetitiveness, tactile sensations, thermal contours, object surfaces, algorithms, equations, configurations, locations of embodiments, additional data, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific code, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 2:
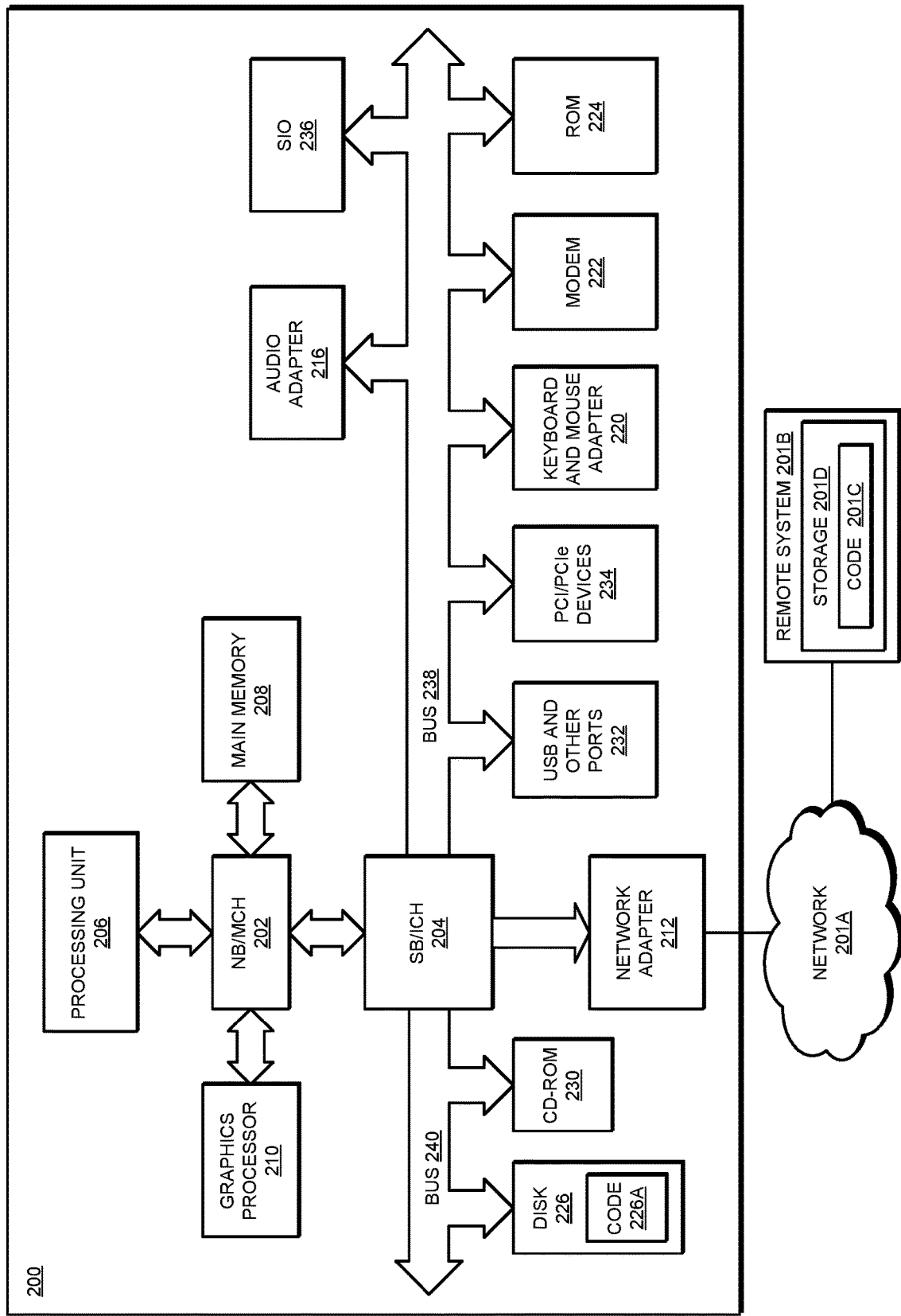
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Server 104 and server 106 couple to network 102 along with storage unit 108. Software applications may execute on any computer in data processing environment 100. Clients 110, 112, and 114 are also coupled to network 102. A data processing system, such as server 104 or 106, or client 110, 112, or 114 may contain data and may have software applications or software tools executing thereon.

Only as an example, and without implying any limitation to such architecture, FIG. 1 depicts certain components that are usable in an example implementation of an embodiment. For example, servers 104 and 106, and clients 110, 112, 114, are depicted as servers and clients only as examples and not to imply a limitation to a client-server architecture. As another example, an embodiment can be distributed across several data processing systems and a data network as shown, whereas another embodiment can be implemented on a single data processing system within the scope of the illustrative embodiments. Data processing systems 104, 106, 110, 112, and 114 also represent example nodes in a cluster, partitions, and other configurations suitable for implementing an embodiment.

Device 132 is an example of a device described herein. For example, device 132 can take the form of a smartphone, a tablet computer, a laptop computer, client 110 in a stationary or a portable form, a wearable computing device, or any other suitable device. Any software application described as executing in another data processing system in FIG. 1 can be configured to execute in device 132 in a similar manner. Any data or information stored or produced in another data processing system in FIG. 1 can be configured to be stored or produced in device 132 in a similar manner.

Application 115 implements an embodiment described herein. Mai device 116 is a modified MAI device in which a hardware modification has been implemented according to an embodiment, and which uses application 115 to operate a software-implemented aspect of an embodiment as described herein.

Servers 104 and 106, storage unit 108, and clients 110, 112, and 114, and device 132 may couple to network 102 using wired connections, wireless communication protocols, or other suitable data connectivity. Clients 110, 112, and 114 may be, for example, personal computers or network computers.

In the depicted example, server 104 may provide data, such as boot files, operating system images, and applications to clients 110, 112, and 114. Clients 110, 112, and 114 may be clients to server 104 in this example. Clients 110, 112, 114, or some combination thereof, may include their own data, boot files, operating system images, and applications. Data processing environment 100 may include additional servers, clients, and other devices that are not shown.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service-oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such as servers 104 and 106, or clients 110, 112, and 114 in FIG. 1, or another type of device in which computer usable program code or instructions implementing the processes may be located for the illustrative embodiments.

Data processing system 200 is also representative of a data processing system or a configuration therein, such as data processing system 132 in FIG. 1 in which computer usable program code or instructions implementing the processes of the illustrative embodiments may be located. Data processing system 200 is described as a computer only as an example, without being limited thereto. Implementations in the form of other devices, such as device 132 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to NB/MCH 202 through an accelerated graphics port (AGP) in certain implementations.

In the depicted example, local area network (LAN) adapter 212 is coupled to South Bridge and I/O controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and I/O controller hub 204 through bus 238. Hard disk drive (HDD) or solid-state drive (SSD) 226 and CD-ROM 230 are coupled to South Bridge and I/O controller hub 204 through bus 240. PCI/PCIe devices 234 may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and I/O controller hub (SB/ICH) 204 through bus 238.

Memories, such as main memory 208, ROM 224, or flash memory (not shown), are some examples of computer usable storage devices. Hard disk drive or solid-state drive 226, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 115 in FIG. 1, are located on storage devices, such as in the form of code 226A on hard disk drive 226, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory 224, or in one or more peripheral devices.

Furthermore, in one case, code 226A may be downloaded over network 201A from remote system 201B, where similar code 201C is stored on a storage device 201D. in another case, code 226A may be downloaded over network 201A to remote system 201B, where downloaded code 201C is stored on a storage device 201D.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub 202. A processing unit may include one or more processors or CPUs.

The depicted examples in FIGS. 1-2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and disk 226 is manifested as a virtualized instance of all or some portion of disk 226 that may be available in the host data processing system. The host data processing system in such cases is represented by data processing system 200.

Figure 3:
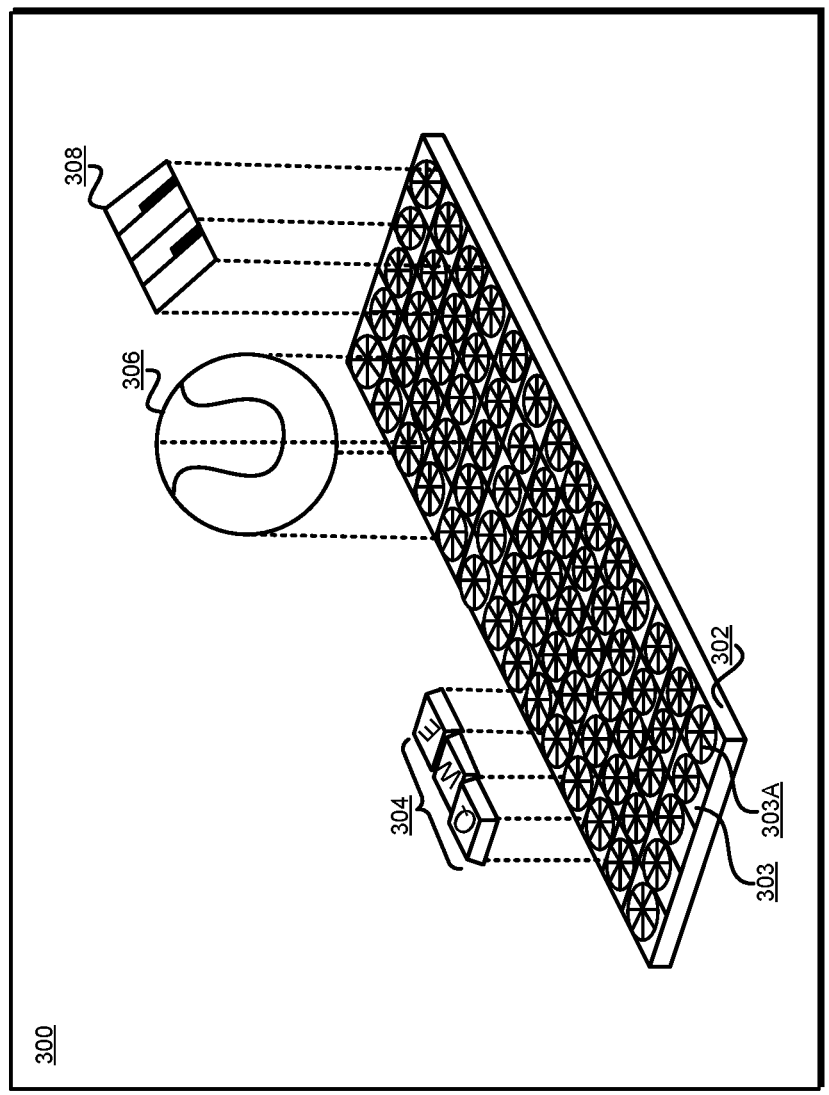
FIG. 3 depicts a block diagram of several example MAIs that are configured and manipulated in accordance with an illustrative embodiment.

With reference to FIG. 3, this figure depicts a block diagram of several example MAIs that are configured and manipulated in accordance with an illustrative embodiment. Mai device 302 is an example of MAI device 116, and includes an array of MAI elements 303. Each MAI element 303 includes a projection nozzle 303A as shown. Mai device 302 further includes one or more SSTs (not visible), one or more thermal elements (not visible), or a combination thereof, in conjunction with one projection nozzles 303A. In one embodiment, an SST, a thermal element, or a combination thereof is associated with a single MAI element 303. In another embodiment, an SST, a thermal element, or a combination thereof is associated with a plurality of MAI elements 303.

Application 115 provides the computational features to operate MAI device 302. For example, application 115 computes a flow rate of a fluid from a infrasonic measurement, instructs an SST to emit or receive a infrasonic signal, instructs a thermal element to activate, causes an operation at MAI device 302 to change a resolution of an air form, compute the locations of the areas participating in a thermal contour, determine the user's thermal likes and dislikes, compute and determine a need for inducing a movement along a thermal contour, and other computation operations as described herein.

These examples of computation operations of a software implementation of all or a part of an embodiment are not intended to be limiting. From this disclosure, those of ordinary skill in the art will be able to determine many other computation operations that can be implemented in software to provide a feature of an embodiment described herein, and the same are contemplated within the scope of the illustrative embodiments.

As one example, a subset of projection nozzles in MAI device 302 can be used to project simulated keyboard keys 304. A key in simulated keys 304 can be touched, tapped, or used in typing in the same manner as a physical key on a physical keyboard.

As another example, a subset of projection nozzles in MAI device 302 can be used to project simulated ball 306. Ball 306 can be touched, gripped, caught, or thrown, or a force can be applied against ball 306 in the same manner as with a physical ball.

As one example, a subset of projection nozzles in MAI device 302 can be used to project simulated piano keys 308. A key in simulated piano keys 308 can be touched, depressed, and released in the same manner as a physical key on a physical piano.

Figure 4:
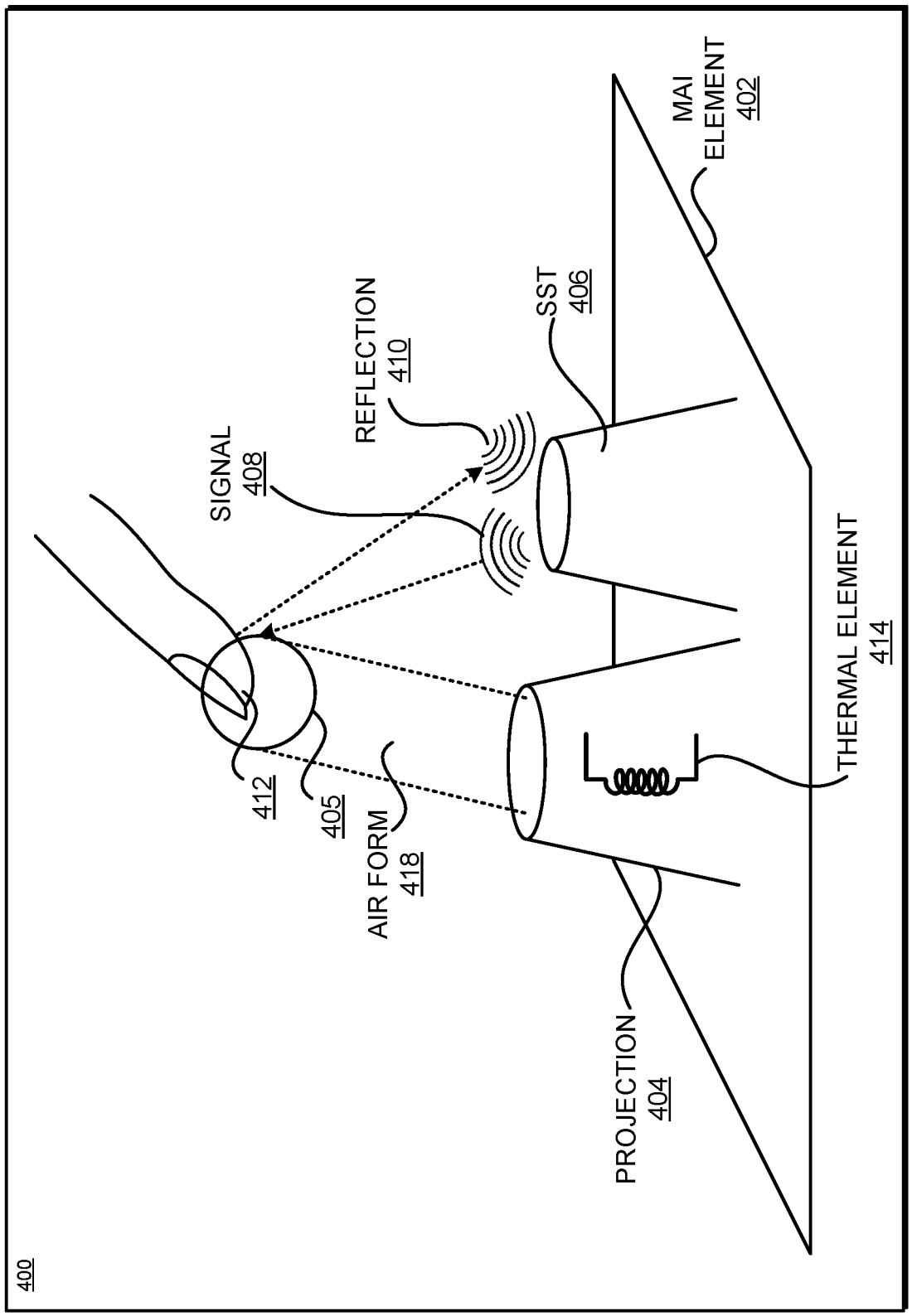
FIG. 4 depicts an example configuration for changing tactile sensitivity of interactions with a midair interface in accordance with an illustrative embodiment.

With reference to FIG. 4, this figure depicts an example configuration for changing tactile sensitivity of interactions with a midair interface in accordance with an illustrative embodiment. Mai element 402 is an example of MAI element 303 in FIG. 3. Projection nozzle 404 is an example of projection nozzle 303A in FIG. 3.

Projection nozzle 404 projects air form 418 to render object surface 405. SST 406 emits infrasonic signal 408 and receives reflected infrasonic signal 410. Signal 408 is directed towards object surface 405. Reflected signal 410 is a reflection of signal 408 from a contact surface manipulating object surface 405. For example, the contact surface may be a portion of finger 412 in tactile contact with object surface 405.

According to one embodiment, SST 406 is collocated with projection nozzle 404 in MAI element 402. According to another embodiment, SST 406 is located outside MAI element 402. SST 406 is depicted adjacent to projection nozzle 404 within MAI element 402 only as a non-limiting example. In another embodiment, SST 406 can be configured within projection nozzle 404. In yet another embodiment, SST 406 and projection nozzle 404 can be one and the same, where a prior-art projection nozzle, e.g., an ultrasonic projection device, has been reconfigured to also emit and receive infrasonic signals.

Thermal element 414 is associated with MAI element 402. According to one embodiment, thermal element 416 is collocated with projection nozzle 404 in MAI element 402. Thermal element 414 is depicted within projection nozzle 404 only as a non-limiting example. In another embodiment, thermal element 414 can be configured adjacent to projection nozzle 404. In yet another embodiment, thermal element 414 can be located outside MAI element 402 but be associated with air form 418 projected from projection nozzle 404.

Figure 5:
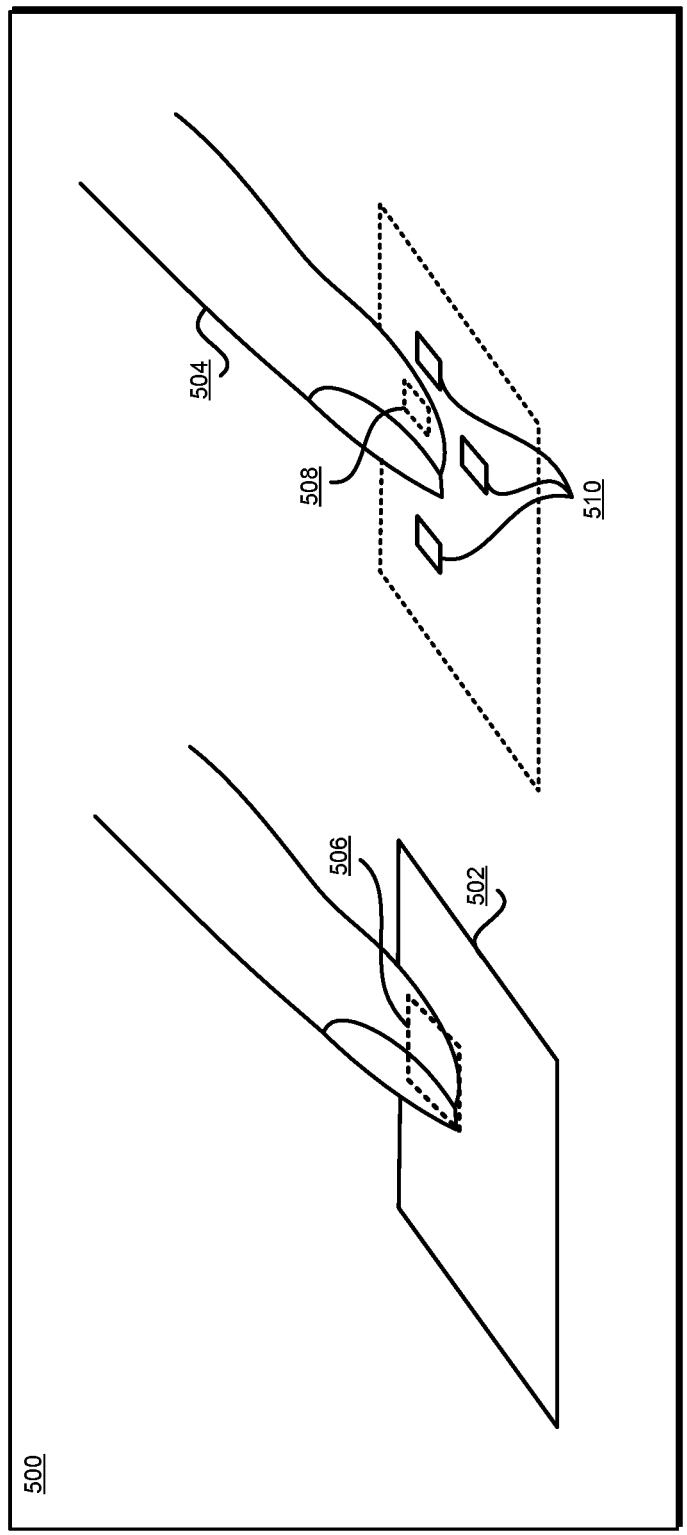
FIG. 5 depicts a resolution change in accordance with an illustrative embodiment.

With reference to FIG. 5, this figure depicts a resolution change in accordance with an illustrative embodiment. Surface 502 is a portion of a surface of a simulated object. Finger 504, as a non-limiting example, contacts surface 502. Area 506 is an area where finger 504 makes contact with surface 502. Area 506 of finger 504 forms the contact surface, and area 506 on surface 502 forms the object surface, such as object surface 405 in FIG. 4.

The number of nerve endings or other tactile sensors in contact surface area 506 on finger 504 is proportional to the size of area 506. As described herein, an embodiment causes a resolution of area 504 in surface 502 to increase. In other words, where finger 504 was previously contacting an area of the size of area 506, the embodiment causes the surface features of area 506 to appear in a comparatively smaller area 508. In one embodiment, the total features occupying area 506 are presented in area 508. In another embodiment, the total features occupying area 506 are divided into feature portions, and different portions made to appear with increased or exaggerated detail within one or more smaller areas, such as using area 508 and one or more other areas 510.

Figure 6:
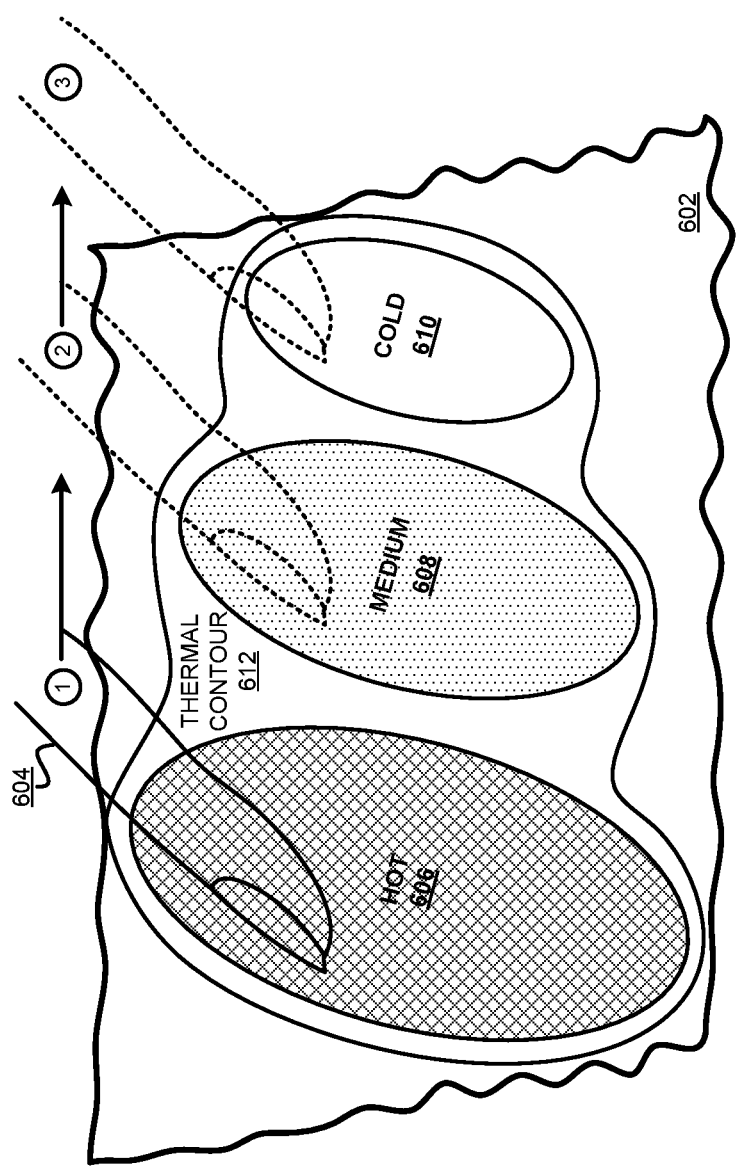
FIG. 6 depicts thermal contouring in accordance with an illustrative embodiment.

With reference to FIG. 6, this figure depicts thermal contouring in accordance with an illustrative embodiment. Surface 602 is an example of surface 502 in FIG. 5. Suppose that finger 604 is positioned in position 1 (shown as circled 1). In position 1, finger 604 is contacting area 606 on surface 602.

An embodiment identifies area 608 and 610 to form thermal contour 612. Assuming that the user dislikes hot surfaces and prefers cold surfaces, the embodiment, such as in application 115, changes the temperature of area 606 to a first temperature where the first temperature is equal to or greater than an upper threshold temperature. Similarly, the embodiment changes the temperature of area 608 to a second temperature where the second temperature is between the upper threshold temperature and a lower threshold temperature. The embodiment changes the temperature of area 610 to a third temperature where the third temperature is equal to or lower than the lower threshold temperature.

Thus, the embodiment constructs temperature contour 612 on surface 602. Temperature contour 612 induces a movement in finger 604 from position 1 to position 2 (depicted as circled 2) and from position 2 to position 3 (depicted as circled 3). The movement of finger 604 is guided by temperature contour from a comparatively hot area 606 through an intermediate temperature area 608 and eventually to a preferred cold temperature area 610.

The example temperature contour comprising three areas of progressively changing temperatures is not intended to be limiting. From this disclosure, those of ordinary skill in the art will be able to adapt an embodiment to form not only temperature contours but other types of movement guidance contours with more or less numbers of areas of differing temperatures, differing shapes, differing textures, differing tactile features, different sonic features, and the like, and such adaptations are contemplated within the scope of the illustrative embodiments.

Figure 7:
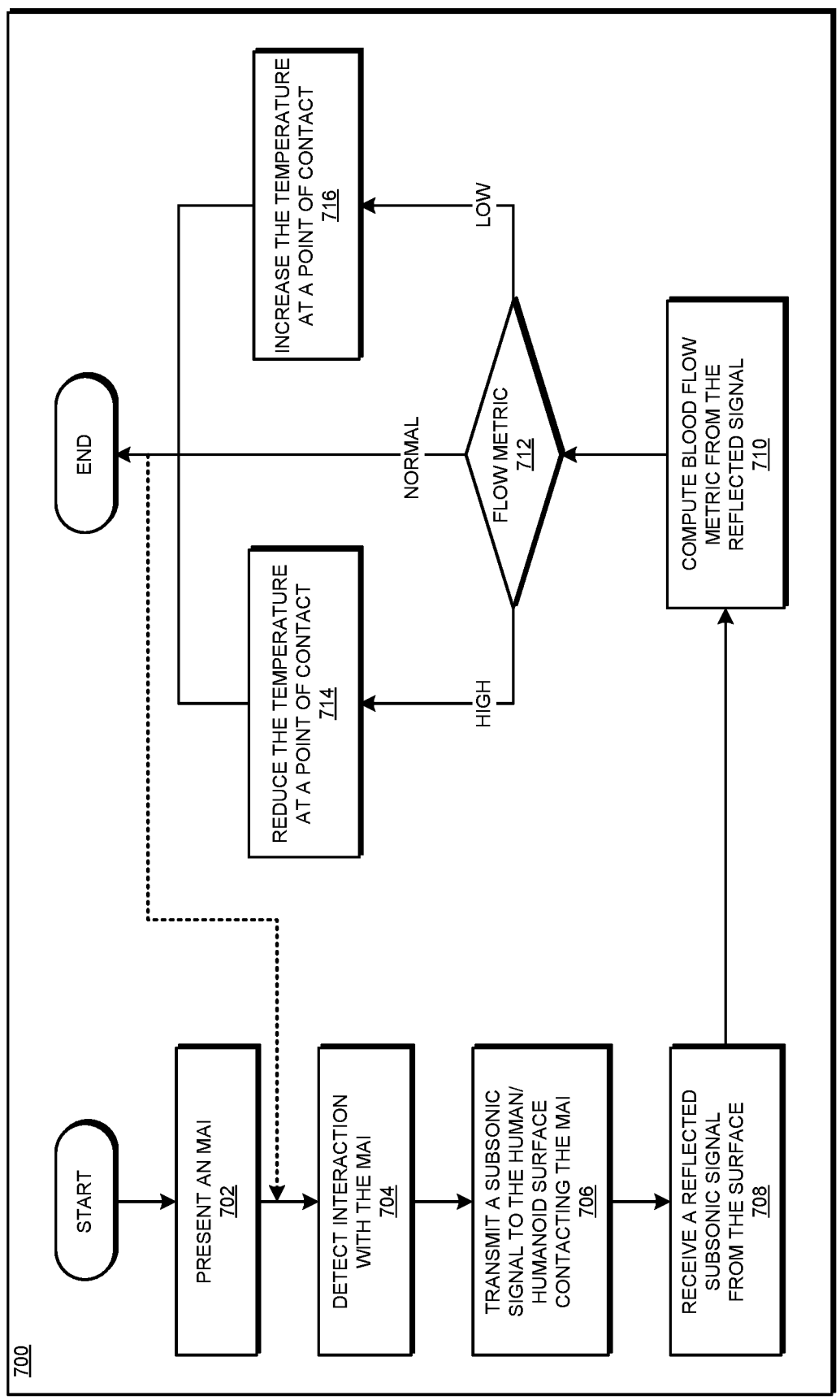
FIG. 7 depicts a flowchart of an example process for changing tactile sensitivity of interactions with a midair interface in accordance with an illustrative embodiment.

With reference to FIG. 7, this figure depicts a flowchart of an example process for changing tactile sensitivity of interactions with a midair interface in accordance with an illustrative embodiment. Process 700 can be implemented in application 115 in FIG. 1.

The application presents an MAI using a modified MAI device (block 702). The application detects a tactile interaction with the MAI (block 704). The application transmits a infrasonic signal to the contact surface (block 706). The application receives a reflected infrasonic signal from the contact surface (block 708).

Using a difference between the transmitted and received infrasonic signals, the application computes a flow metric (block 710). The flow metric is indicative of an amount of blood flow at the contact surface.

If the flow metric indicates a high flow ("High" path of block 712), the application reduces the temperature of the simulated surface at a point or area of contact (block 714). The application ends process 700 thereafter.

If the flow metric indicates a low flow ("Low" path of block 712), the application increases the temperature of the simulated surface at a point or area of contact (block 716). The application ends process 700 thereafter.

If the flow metric indicates a normal flow ("Normal" path of block 712), the application leaves the temperature of the simulated surface at a point or area of contact unchanged. The application ends process 700 thereafter.

With reference to FIG. 8, this figure depicts a flowchart of another example process for changing tactile sensitivity of interactions with a midair interface in accordance with an illustrative embodiment. Process 800 can be implemented in application 115 in FIG. 1.

The application presents an MAI (block 802). The application detects an interaction occurring with the MAI (block 804). The application performs a tetanic classification of the interaction, such as by classifying the interaction according to a rapidity of touch, rapidity of a change in the pressure of a touch, the speed of repetition of the touch, the repetition of a motion in the touch, or some combination thereof (block 806).

If the tetanic classification is acceptable ("No" path of block 808), the application does not induce a movement in the user's extremity and ends process 800 thereafter. If the tetanic classification is unacceptable ("Yes" path of block 808), the application induces a movement in the user's extremity by either forming a temperature contour on the simulated surface (block 810), changing a resolution of the object surface (block 812), or both. The application ends process 800 thereafter.

Thus, a computer implemented method, system or apparatus, and computer program product are provided in the illustrative embodiments for changing tactile sensitivity of interactions with a midair interface and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, including but not limited to computer-readable storage devices as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
    capturing a reflection of an infrasonic signal, the infrasonic signal being reflected by a contact surface, wherein the contact surface is contacting a simulated surface of an object projected from a midair interface (MAI) device;
    converting a difference between the infrasonic signal and the reflection into a measurement of a flow in the contact surface, wherein the flow in the contact surface is a rate of blood flow in a capillary at the contact surface; and
    causing, responsive to the measurement being in a range of measurements, a change in a first temperature of a volume of a medium, the simulated surface being projected in volume of the medium, wherein the change in the first temperature causes a second change in the flow in the contact surface.

2. The method of claim 1, further comprising:
    detecting, from the measurement, a reduction in tactile sensitivity of the contact surface, wherein the flow in the contact surface is a rate of blood flow in a capillary at the contact surface, and wherein a first value of the measurement of the flow corresponds to a rate of the blood flow being below a first threshold, the first value being indicative of a reduction in tactile sensitivity;
    determining a first area and a position of the first area on the simulated surface where the contact surface is contacting the simulated surface, and wherein a simulated feature is subjected to the contacting;
    increasing a resolution of the simulated feature to a first resolution by simulating the simulated feature in a second area, wherein the second area occupies the position, the first resolution compensates for the reduction in the tactile sensitivity.

3. The method of claim 1, further comprising:
    detecting a repetition of the contacting;
    responsive to a surface temperature less than a first threshold value, changing a second temperature of a first area on the simulated surface where the contact surface is contacting the simulated surface;
    changing a third temperature of a second area on the simulated surface above a second threshold value, the first area of the surface temperature less than a first threshold value and the third temperature of a second area above a second threshold value forming a temperature contour on the simulated surface;
    inducing a movement of the contact surface from the first area to the second area using the temperature contour.

4. The method of claim 1, further comprising:
coupling, to cause the change in the first temperature of the volume of the medium, a thermal element with the MAI device, the thermal element being configured to increase a fourth temperature of an air form being projected, the air form projecting a portion of the simulated surface where the contact surface is contacting the simulated surface.

5. The method of claim 4, further comprising:
configuring the thermal element in an element of the MAI device, wherein the element projects the portion of the simulated surface.

6. The method of claim 4, further comprising:
modifying a projection nozzle of an element of MAI device to cause the change in the fourth temperature, wherein the projection nozzle projects the portion of the simulated surface.

7. The method of claim 1, wherein a first value of the measurement of the flow corresponds to a rate of the blood flow being below a first threshold, the first value being indicative of a reduction in tactile sensitivity due to the rate of blood flow in the capillary below the first threshold.

8. The method of claim 7, further comprising:
increasing, as a part of changing the first temperature to a fifth temperature, the fifth temperature restoring the tactile sensitivity in the contact surface.

9. The method of claim 1, wherein a second value of the measurement of the flow corresponds to a rate of the blood flow being above a second threshold, the second value being indicative of a reduction in tactile sensitivity.

10. The method of claim 9, further comprising:
decreasing, as a part of changing the first temperature to a sixth temperature, the sixth temperature restoring the tactile sensitivity in the contact surface.

11. The method of claim 1, further comprising:
coupling an infrasonic transmitter with the MAI device, the infrasonic transmitter directing the infrasonic signal to the contact surface; and
coupling an infrasonic receiver with the MAI device, the infrasonic receiver receiving the reflection of the infrasonic signal from the contact surface.

12. The method of claim 11, further comprising:
configuring the infrasonic transmitter and the infrasonic receiver in an element of the MAI device, wherein the element projects a portion of the simulated surface, the contact surface contacting the portion.

13. The method of claim 11, further comprising:
modifying a projection nozzle of an element of MAI device to transmit the infrasonic signal and receive the reflection, wherein the projection nozzle projects a portion of the simulated surface, the contact surface contacting the portion.

14. The method of claim 1, wherein the simulated surface of the object is projected using ultrasound.

15. The method of claim 1, wherein the simulated surface of the object is projected using columns of air, a first column having a first controllable pressure and a second column having a second controllable pressure.

16. A computer usable program product comprising a computer-readable storage device, and program instructions stored on the storage device, the stored program instructions comprising:
program instructions to capture a reflection of an infrasonic signal, the infrasonic signal being reflected by a contact surface, wherein the contact surface is contacting a simulated surface of an object projected from a midair interface (MAI) device,
program instructions to convert a difference between the infrasonic signal and the reflection into a measurement of a flow in the contact surface, wherein the flow in the contact surface is a rate of blood flow in a capillary at the contact surface; and
program instructions to cause, responsive to the measurement being in a range of measurements, a change in a temperature of a volume of a medium, the simulated surface being projected in volume of the medium, wherein the change in the temperature causes a second change in the flow in the contact surface.

17. The computer usable program product of claim 16, wherein the computer usable code is stored in a computer readable storage device in a data processing system, and wherein the computer usable code is transferred over a network from a remote data processing system.

18. The computer usable program product of claim 16, wherein the computer usable code is stored in a computer readable storage device in a server data processing system, and wherein the computer usable code is downloaded over a network to a remote data processing system for use in a computer readable storage device associated with the remote data processing system.

19. A computer system comprising a processor, a computer-readable memory, and a computer-readable storage device, and program instructions stored on the storage device for execution by the processor via the memory, the stored program instructions comprising
program instructions to capture a reflection of an infrasonic signal, the infrasonic signal being reflected by a contact surface, wherein the contact surface is contacting a simulated surface of an object projected from a midair interface (MAI) device,
program instructions to convert a difference between the infrasonic signal and the reflection into a measurement of a flow in the contact surface, wherein the flow in the contact surface is a rate of blood flow in a capillary at the contact surface; and
program instructions to cause, responsive to the measurement being in a range of measurements, a change in a temperature of a volume of a medium, the simulated surface being projected in volume of the medium, wherein the change in the temperature causes a second change in the flow in the contact surface.

* * * * *